Figure 1:
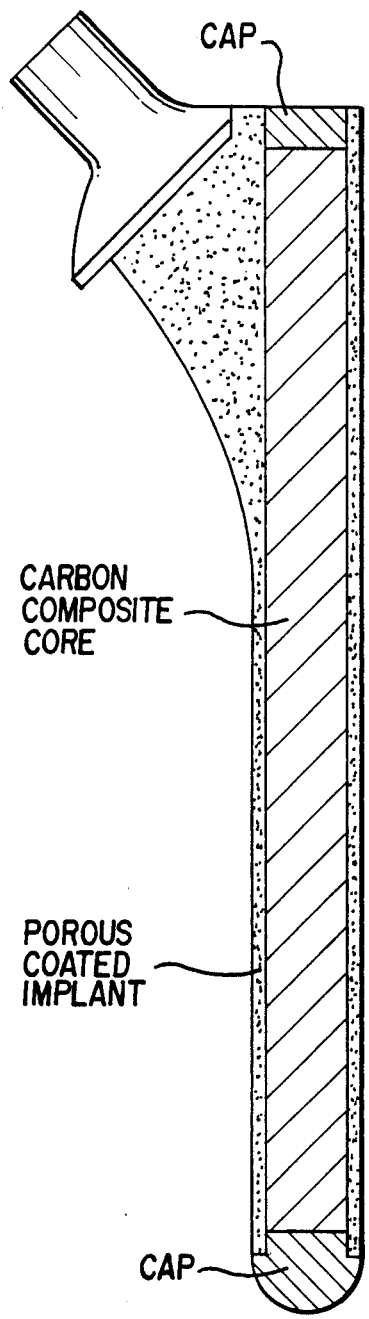

United States Patent [19]

Bobyn

[11] Patent Number: 4,978,358
[45] Date of Patent: Dec. 18, 1990

[54] ORTHOPAEDIC PROSTHETIC DEVICE POSSESSING IMPROVED COMPOSITE STEM DESIGN

[75] Inventor: John D. Bobyn, Annandale, Va.

[73] Assignee: Zimmer Inc., Warsaw, Ind.

[21] Appl. No.: 368,896

[22] Filed: Jun. 21, 1989

Related U.S. Application Data

[63] Continuation of Ser. No. 253,444, Oct. 6, 1988, abandoned, which is a continuation of Ser. No. 873,718, Jun. 12, 1986, abandoned.

[51] Int. Cl.$^5$ ............................................. A61F 2/32
[52] U.S. Cl. ...................................................... 623/23
[58] Field of Search ..................... 623/16, 18, 19, 20, 623/21, 22, 23, 66

[56] References Cited

U.S. PATENT DOCUMENTS

| | | | |
|---|---|---|---|
| 3,707,006 | 12/1972 | Bokros et al. | 623/16 |
| 3,846,846 | 11/1974 | Fischer | 623/23 |
| 3,893,196 | 7/1975 | Hochman | 623/23 |
| 3,906,550 | 9/1975 | Rostoker et al. | 623/23 |
| 4,221,623 | 9/1980 | Heissler et al. | 623/23 |
| 4,287,617 | 9/1981 | Tornier | 623/23 |
| 4,336,618 | 6/1982 | Raab . | |
| 4,479,271 | 10/1984 | Bolesky et al. | 623/18 |
| 4,655,777 | 4/1987 | Dunn | 623/23 |
| 4,718,914 | 1/1988 | Frey et al. | 623/23 |

OTHER PUBLICATIONS

Advances in Orthopaedic Surgery Copyright 1983 by the Williams & Wilins Co.

"Biologic Fixation of Hip Orostheses: Review of the Clinical Status and Current Concepts" by J. Dennis Bobyn, Ph.D. and Charles A. Engh, M.D.

The Cementless Fixation of Hip Endoprostheses, "The Use of Carbon as an Implant Material" by W. Huttner and K. J. Huttinger, pp. 81-94.

Orthopedics Sep. 1984, vol. 7/No. 9, "Human Histology of the Bone-Porous Metal Implant Interface" by J. Dennis Bobyn, Ph.D. and Charles A. Engh, M.D.

Primary Examiner—David J. Isabella
Attorney, Agent, or Firm—Stevens, Davis, Miller & Mosher

[57] ABSTRACT

A surgical prosthetic device or implant comprising a composite structure with an outer metallic component and a separate inner component comprised of the same or a different material. The outer component may be made of commercially pure titanium or a titanium alloy or of a cobalt-based alloy. The inner component may be made of a carbon composite material that may be reinforced or not reinforced with a polymeric material.

2 Claims, 2 Drawing Sheets

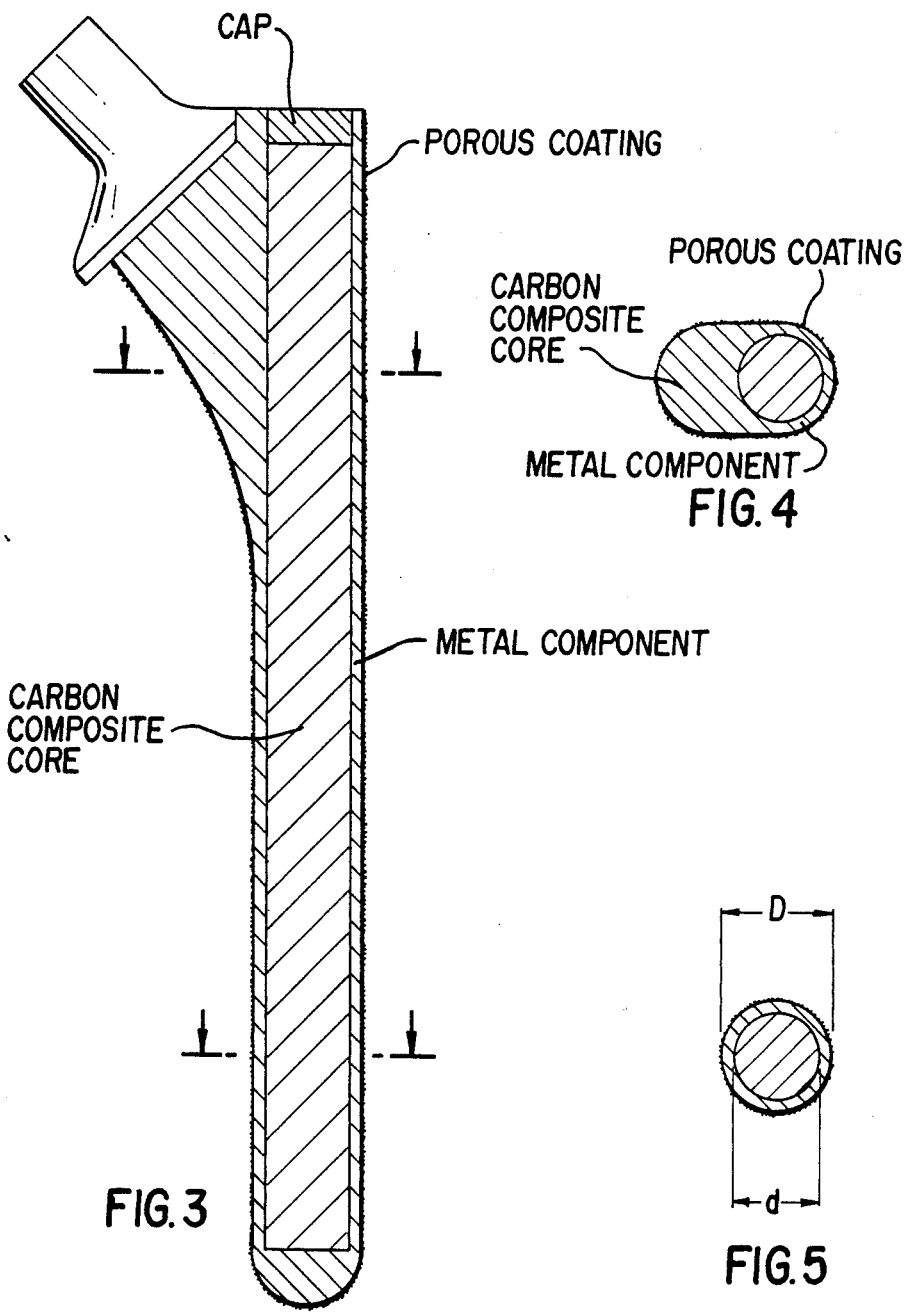

ORTHOPAEDIC PROSTHETIC DEVICE POSSESSING IMPROVED COMPOSITE STEM DESIGN

This application is a continuation of application Ser. No. 253,444, filed Oct. 6, 1988 now abandoned, which in turn is a continuation of application Ser. No. 873,718, filed June 12, 1986 now abandoned.

FIELD OF THE INVENTION

This invention relates in general to orthopaedic devices fabricated from two or more materials that combine to provide high strength properties and biomechanical compatibility with bone. In one aspect, this invention relates to such devices having an outer metallic component with a porous coating or surface texture for fixation by tissue ingrowth and an inner composite material core for providing increased mechanical strength and reduced rigidity. The invention is described in the context of orthopaedic prostheses that replace the femoral side of the hip joint but it can also be extended to prostheses that replace other joints such as the knee, the elbow, and the shoulder.

BACKGROUND OF THE INVENTION

Prior to the present invention, various types of prosthetic devices have been used for the treatment of various orthopaedic problems. Joint replacement prostheses have generally been manufactured from solid metal, for reasons of strength, and recent designs perform very well with very few cases of mechanical failure. One of the problems with solid metal implants is that their high rigidity in relation to bone can result in preferential stress transfer through the implant and away from the bone in which the implant functions. The consequence of decreased stress and strain in bone adjacent to an implant is resorptive remodeling of bone in accordance with the principles described by Wolff and Koch (Wolff, J: Das Gesetz des Transformation der Knochen. Berlin: Hirschwald, 1892; and Koch, J. L.: The Laws of Bone Architecture, Amer. J. Anat. 21:177, 1917). Loss of bone stock adjacent to a successful implant is of clinical concern and can represent a serious problem if the bone loss impairs the support and function of the implant or limits the scope of subsequent operative procedures should they ever become necessary. This problem of loss of bone stock adjacent to an implant worsens with increasing implant rigidity. Thus, the tendency for and extent of bone loss tends to increase with the use of stiffer implant materials and larger implant sizes.

To address this problem, orthopaedic implants such as joint replacement prostheses for the hip have been manufactured from two or more materials that combine to reduce the implant rigidity. One example is the "isoelastic" femoral stem designed in the early 1970's by Mathys (Mathys, R.: Stand der Verwendung von Kunststoffen fur Kunstliche Gelenke, Aktuel Traumatol., 3:253, 1973; and Mathys, R., and Mathys, R., Jr.: The Use Of Polymers For Endoprosthetic Components, in The Cementless Fixation of Hip Endoprostheses, (Morscher, E., ed.), Springer-Verlag, Berlin, 1984). It consists of an inner metal rod embedded in polyacetyl resin. The material thicknesses and properties are adjusted to render the stem similar to the femur in terms of bending stiffness. Another example is a stem with a metal core and a porous polysulfone outer surface (Demane, M., Roberson, J. R., Greenwood, K. M., Riggins, R. S., and Spector, M.: Porous Polysulfone-Coated Femoral Stems, in ASTM symposium on quantitative characterization and performance of porous implants for hard tissue applications, 1986, In press; Spector, M., Davis, R. J., Lunceford, E. M., Harmon, S. L.: Porous Polysulfone Coatings For Fixation of Femoral Stems by Bone Ingrowth, Clin. Orthop. 176:34, 1983; Spector, M., et al: Prosthetic Devices Having Coatings Of Selected Porous Bioengineering Thermoplastics. U.S. Pat. No. 4,164,794. Aug. 1979). The low stiffness of the porous polysulfone allows the manufacture of a stem with lower bending stiffness than a solid metal stem of the same dimensions. Another example is a femoral implant comprised entirely of carbon fiber reinforced composite material (Huttner, W., and Huttinger K. J.: The Use of Carbon as an Implant Material, in The Cementless Fixation of Hip Endoprostheses, (Morscher, E., ed.), Springer-Verlag, Berlin, 1984, pages 81–94; Rettig, H., and Weber, U.: Experimental and Clinical Experience With Carbon Hip Endoprostheses, in the Cementless Fixation of Hip Endoprostheses, (Morscher, E., ed.), Springer-Verlag, Berlin, 1984; and Harms, J., Mittelmeier, H., and Mausle, E.: Results of Animal Studies on the Use of Carbon Fiber-Reinforced Plastic Prostheses, in The Cementless Fixation of Hip Endoprostheses, (Morscher, E., ed.), Springer-Verlag, Berlin, 1984). With this type of design the material properties may be adjusted to render the stem more biomechanically compatible with the femur.

All of these designs possess inherent disadvantages. A common disadvantage is that the material which interfaces with bone (polymer or carbon composite) is susceptible to fretting wear against bone and the production of particulate material. The precise consequences of this from a biological perspective are not fully known. It is known, however, based on the results of studies of particulate foreign material placed in soft tissue sites in lower animals, that such material can elicit negative biological response in the form of foreign body giant cell inflammatory reactions or even neoplastic change. It is also known that polymeric wear debris generated from the articulating surfaces of joint replacement prostheses may cause soft tissue inflammatory granulomatous reactions and even bone resorption reaction which can lead to implant loosening (Buchhorn, G. H., and Willert, H. G.: Effects of Plastic Wear Particles on Tissue, in Biocompatibility of Orthopaedic Implants. Volume I, (Williams, D. F., ed.), CRC Press, Florida, 1982). In general, compared with surgical implant metals such as cobalt- and titanium-based alloys, polymeric and carbon materials are more prone to breakdown due to relative motion against bone during implant loading, may demonstrate poorer compatibility when interfaced directly with bone, and are not as well tested or understood when interfaced directly with osseous tissue because they have a much shorter history of clincial use.

A specific disadvantage with the "isoelastic" design is that the relatively small inner metal core is prone to mechanical failure. A specific disadvantage with the porous polysulfone-coated design is that the bond strength between the porous coating and the substrate is weaker than that which can be achieved by bonding porous metal to a metal substrate (Demane, M., Roberson, J. R., Greenwood, K. M., Riggins, R. S., and Spector, M.: Porous Polysulfone-Coated Femoral Stems, in ASTM symposium on quantitative characterization and performance of porous implants for hard tissue applications, 1986, in press; Pilliar, R. M., Cameron, H. U., Macnab, I.: Porous-Surfaced Layered Prosthetic Devices, J. Biomed. Eng., 10:126, 1975; and Pilliar, R. M.: Surgical Prosthetic Device With Porous Metal Coating. U.S. Pat. No. 3,855,638. Dec., 1974). A specific disadvantage with the carbon composite design is the inability to incorporate a porous surface of the type that has proven to be so efficacious for bone ingrowth fixation and long term implant stability.

Prior to the present invention, various methods have been disclosed in the literature for the attachment of prosthetic devices to the musculoskeletal system. These methods can generally be classified into those involving impaction, nails and screws, bone cement, and porous surface materials. Current interest is increasingly being focused on porous-surfaced implants designed for fixation by tissue ingrowth as representing a viable solution to the problem of late implant loosening, the most prevalent problem in joint replacement surgery using simple impaction or cementing fixation techniques. There are several types of porous materials and methods for their fabrication that have been disclosed in the literature (Pilliar, R. M.: Surgical Prosthetic Device With Porous Metal Coating. U.S. Pat. No. 3,855,638. Dec., 1974; Pilliar, R. M.: Surgical Prosthetic Device Or Implant Having Pure Metal Porous Coating. U.S. Pat. No. 4,206,516. June, 1980; Smith, L. W. et al: Prosthetic Parts and Methods of Making the Same. U.S. Pat. No. 3,314,420. Apr., 1967; Wheeler, K. R., Supp, K. R., Karagianes, M. T.: Void Metal Composite Material and Method. U.S. Pat. No. 3,852,045. Dec. 3, 1974; Frey, O.: Anchoring Surface For a Bone Implant. U.S. Pat. No. 4,272,855. June, 1981; Spector, M., et al: Prosthetic Devices Having Coatings of Selected Porous Bioengineering Thermoplastics. U.S. Pat. No. 4,164,794. Aug., 1979; Homsy, C.: U.S. Pat. No. 3,971,670. July, 1976; Tronzo, R.: U.S. Pat. No. 3,808,606. May, 1974; Sauer, B.: U.S. Pat. No. 3,986,212. Oct., 1976; and Hahn, H.: Bone Implant. U.S. Pat. No. 3,605,123. Sept., 1974). These can generally be grouped into porous polymers and porous metals. As described earlier, the porous polymers offer the advantage of allowing fabrication of a stem with lower rigidity. Their disadvantages are their generally weaker mechanical properties, their poorer biocompatibility, and their much shorter history of clinical use.

Metal implants with metal porous surfaces can be fabricated either by casting the porous surface integrally with the implant or adding the porous surface after implant casting. The method used for producing the latter type of porous surface is generally preferred because it permits more control and optimization of pore characteristics for the process of tissue ingrowth. A porous metal surface is generally added to the substrate by techniques involving high temperature diffusion bonding (Pilliar, R. M., Cameron, H. U., Macnab, I.: Porous-Surfaced Layered Prosthetic Devices. J. Biomed. Eng., 10:126, 1975; Pilliar, R. M.: Powder Metal-Made Orthopaedic Implants With Porous Surface For Fixation By Tissue Ingrowth. Clin. Orthop. 176:42, 1983; Pilliar, R. M.: Surgical Prosthetic Device With Porous Metal Coating. U.S. Pat. No. 3,855,638. Dec., 1974; and Pilliar, R. M.: Surgical Prosthetic Device or Implant Having Pure Metal Porous Coating. U.S. Pat. No. 4,206,516. June, 1980). This allows fabrication of an implant with a high strength porous coating and a coating-substrate bond strength that is stronger than achievable with porous polymer coatings (Demane, M., Roberson, J. R., Greenwood, K. M., Riggins, R. S., and Spector, M.: Porous Polysulfone-Coated Femoral Stems, in ASTM symposium on quantitative characterization and performance of porous implants for hard tissue applications, 1986, in press; Pilliar, R. M., Cameron, H. U., Macnab, I.: Porous-Surfaced Layered Prosthetic Devices. J. Biomed. Eng., 10:126, 1975; and Pilliar, R. M.: Surgical Prosthetic Device With Porous Metal Coating. U.S. Pat. No. 3,855,638. Dec., 1974). Unfortunately, the high temperature heat treatment results in microstructural change in the implant substrate which reduces the mechanical properties of the substrate material (Pilliar, R. M.: Powder Metal-Made Orthopaedic Implants With Porous Surface for Fixation By Tissue Ingrowth. Clin. Orthop. 176:42, 1983). Thus, conventional surgical grade cobalt-based alloys as well as conventional surgical grade titanium-based alloys, the two most commonly used materials for such applications, are adversely affected by adding a porous coating.

This has not precluded the clinical use of such porous coated implants (Engh, C. A., and Bobyn, J. D.: Biological Fixation in Total Hip Arthroplasty. Slack Inc., Thorofare, New Jersey, 1985). It is believed that the loss of strength of the cobalt-based alloy is tolerable (<15%) and the implants used are large enough to possess adequate static and fatigue properties. Unfortunately, although larger stems are stronger they are also more rigid and thus increase the potential for stress-mediated bone loss. The preferred alternative to cobalt-based implant alloy is titanium-based implant alloy because of its lower stiffness and higher biocompatibility relative to cobalt-based alloy. However, titanium alloy is particularly notch-sensitive, meaning that cyclic loading tends to cause crack initiation at the junction of the porous material and the implant substrate. The cracks can propagate through the implant and eventually cause fatigue fracture. To overcome this problem, implant manufacturers add the porous coating by sintering at a lower temperature to reduce the strength loss in the substrate material and/or confine the porous coating to the upper or proximal portion of the stem, away from lower regions of high tensile stress which could precipitate crack initiation. Thus, the preferred titanium alloy can be used in porous-coated form if the method of manufacture is altered or the latitude in placement of the porous coating is restricted. Both these factors, however, can lead to problems. The lower sintering termperature complicates and increases the cost of manufacture and can result in a weaker bond strength between the porous coating and the substrate. Also, from a surgical perspective it is often preferred to use an implant with porous coating on the majority, not the minority of the stem length, to ensure superior clinical results. To summarize, while titanium alloy is preferred because of its lower stiffness and higher biocompatibility than cobalt alloy, the application of a porous coating can cause problems with manufacture and implant strength. While cobalt alloy can be porous-coated over any portion of the implant, it possesses inferior biocompatibility and is about 1.7 times stiffer than titanium alloy, thus increasing the potential for bone loss by stress shielding.

Considering all of these factors, it can be summarized that:

1. The concept of using a stem with flexural rigidity closer to bone than can be achieved by using solid metal is desirable for reasons of optimizing stress transfer and minimizing stress-mediated resorptive bone change.

2. But, the materials and designs currently utilized to achieve this result suffer disadvantages.

3. The concept of using a porous metal coated implant for implant fixation by tissue ingrowth is desirable for the achievement of permanent implant stability.

4. But, the preferred method of porous metal coated implant fabrication reduces implant strength, and/or choice of the preferred implant material, and/or latitude in placement of the porous coating.

SUMMARY OF THE INVENTION

In accordance with the present invention, therefore, there is provided a novel and improved structure that optimizes the advantages and minimizes the disadvantages of the implant designs just described. Specifically, the invention is an implant with composite material construction consisting of:

1. An outer component fabricated from metal. In a preferred embodiment the metal is a commercially pure surgical grade titanium or titanium-based surgical implant alloy that is porous-coated according to one of the techniques previously described in the literature, and 2. An inner component or core fabricated from a material of lower bending stiffness and/or higher strength than the outer metal. In a preferred embodiment, the inner reinforcing material is a carbon fiber reinforced composite.

It is appropriate to note that the inner core of reinforcing material can be chosen to possess fatigue properties at least equal to those of implant metal that has not suffered a decrease in strength due to the sintering process used to bond the porous coating to the substrate (Huttner, W., and Huttinger, K. J.: The Use of Carbon as an Implant Material, in The Cementless Fixation of Hip Endoprostheses, (Morscher, E., ed.), Springer-Verlag, Berlin, 1984, pages 81–94). Thus, the inner core material can provide sufficient fatigue strength to preclude complete implant failure regardless of the mechanical integrity of the outer metal component. At the same time, the inner core of reinforcing material may be chosen so as to possess a bending stiffness that is several times lower than that of the metal it replaces (Huggner, W., and Huttinger, K. J.: The Use of Carbon as an Implant Material, in The Cementless Fixation of Hip Endoprostheses, (Morscher, E., ed.), Springer-Verlag, Berlin, 1984, pages 81–94). Thus, the inner component of the implant may be chosen to be both strong and flexible, in relative terms, both of which are preferred characteristics as alluded to in the preceding text. The outer component is metal and it may serve as a substrate for a porous metal coating; both of these characteristics are preferred from biocompatibility and fixation perspectives. Also preferred is that commercially pure titanium or titanium alloy is used for the outer material and this may be porous-coated to any extent since the mechanical integrity of the implant as a whole does not depend entirely on the strength characteristics of its metal component.

It is to be understood that the core component may consist of one or more materials. Thus, the core material need not consist solely of carbon fiber reinforced composite material. It may consist of any of a number of engineering materials recognized in the art as suitable for the purposes of strength reinforcement and/or decreased implant rigidity. It may even consist of the same metal used for fabrication of the outer component, but in high strength form, unaffected by the heat treatment utilized to attach or impart the porous surface. Thus it may be preferred to choose a material whose properties only provide for overall increased implant mechanical strength. Alternatively, it may be preferred to choose a material whose properties only provide for overall decreased implant rigidity. The material chosen for the core is preferably one which possesses proven biocompatibility, i.e., accepted tolerance when exposed to body tissues and fluids. It is to be understood, however, that the core material may be one without tested or proven biocompatibility as a surgical implant material because the implant may be so fabricated that the core material is at no risk of exposure to the body.

It is to be understood that the outer component does not have to be comprised of pure titanium or titanium surgical implant alloy. It may be comprised of any of a variety of accepted surgical implant metals such as cobalt-based alloys. It is also to be understood that the outer component does not have to be porous coated by a high temperature heat treatment involving diffusion bonding. The porous coating may be applied by any of the techniques currently described in the literature or by any other technique deemed suitable for the intended function of the implant. Thus, the surface of the outer metallic component may be rendered suitable for tissue ingrowth fixation by methods involving plasma spraying or casting. The surface of the outer metallic component may be roughened or textured or surface-relieved by methods such as etching, sand blasting, mechanical removal of material, or any other process that renders the surface other than smooth along any part or all of its entirety. It is to be understood that the surface of the outer metallic component may be left essentially smooth, if desired, as would be the case for an implant designed for fixation by simple press fit or impaction. It is to be understood that the outer metal component is relatively thick in its thinnest dimension and therefore possesses substantial inherent strength. That is, the wall thickness of the outer metal component is at least about 0.20 to 0.25 millimeters. This distinguishes this invention from one in which a core implant material is merely coated with a thin layer of a second material, measured in microns of thickness, by techniques such as plasma deposition or dipping, as a method of masking the underlying material without actually providing substantial structural strength. It is also to be understood that the relatively thick outer metallic surface may be coated with such a thin layer of another material as is done with certain carbon and ceramic materials to render the surface more biocompatible or conducive for the apposition or ingrowth of tissue (Shaw, B. J., and Miller, P.: Sputtering Of Bone on Prostheses. U.S. Pat. No. 3,918,100. Nov., 1975; Aoyagi, M., et al: Implants For Bones, Joints, and Tooth Roots. U.S. Pat. No. 4,146,936. Apr., 1979; Shikita, T., and Kadaguchi, S.: Prosthetic Substituted Member For Living Body and a Method For The Surgical Treatment By Use Thereof. U.S. Pat. No. 4,336,617. June, 1982; and Hench, L. L.: Method of Bonding a Bioglass to Metal. U.S. Pat. No. 4,159,358. June, 1979). It is to be understood that the maximum thickness of the wall of the outer metal component varies with the degree to which it is desired to structurally reinforce and provide greater overall implant flexibility through the addition of the core material. Generally, the maximum thickness of the thinnest portion of the outer metal component is normally between 2 and 3 millimeters.

The accompanying drawings illustrate, by way merely of example, preferred embodiments of a device according to the invention.

Figure 2:
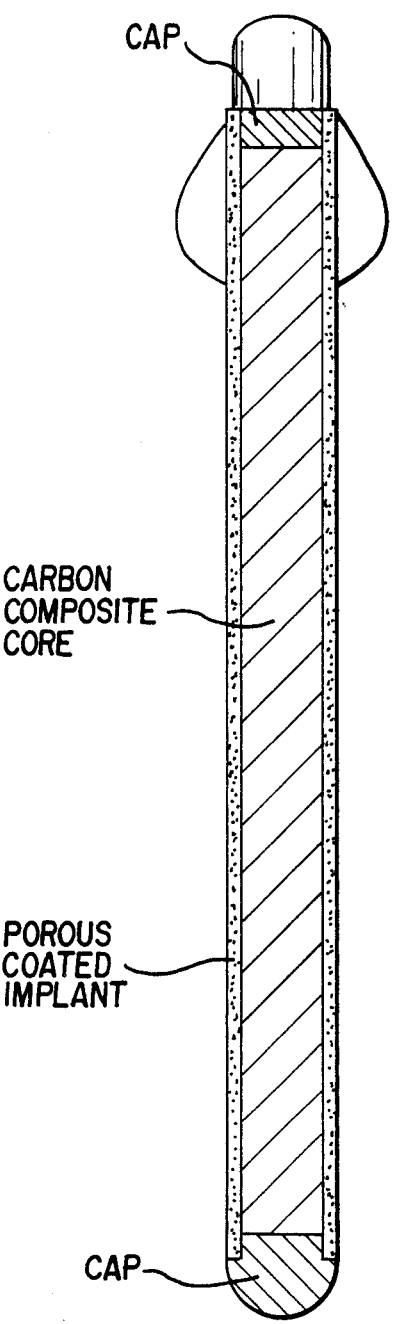

FIGS. 1 and 2 show front and side views of a prosthetic device of the present invention. FIG. 3 shows another embodiment, while FIGS. 4 and 5 show cross-sections of the embodiment of FIG. 3.

The illustrated member is a femoral implant for total hip replacement. The stem is straight and cylindrical in its lower portion. A cylindrical core of carbon composite material is contained within an outer metallic component. The illustrated member may be manufactured by the following process. The stem may be cast or forged in conventional form out of solid metal. In a second step, the cylindrical hollow may be fashioned by progressive drilling procedures. In a third step, the outer surface of the metal component may be porous-coated according to one of the procedures described in the literature. The core of carbon composite may be manufactured with appropriate tolerances in a separate procedure. The composite core may be inserted to fill the hollow metal implant. In a final step, the open end or ends of the implant may be suitably sealed by caps made of a suitable material such as metal or a polymeric material; if metal is employed for making the cap, this should be the same metal as the metal of the stem of the implant so as to avoid the creation of an electrocouple effect in the patient's body.

It should be understood that the implant does not have to be manufactured according to the described method. It may be manufactured according to any other method so chosen as to obtain a metallic implant with an inner core of material that is either different than the metal or added as a separate step in the fabrication process. It should be understood that the femoral implant does not have to possess the same overall illustrated shape. It should also be understood that the core material does not have to possess a cylindrical shape or a shape that is symmetrical about any axis. It should also be understood that the core material may fill any part or all of the hollow portion of the stem.

The biomechanical advantage offered by an implant fabricated according to this invention may be illustrated by comparison of its bending stiffness (in the cylindrical portion of the stem) with that of a conventional solid metal implant. By way of example, consider the following implant dimensions and numerical relationshipS. The illustrated device possesses an outer diameter D in the lower cylindrical portion of 18 millimeters. The inner diameter d of the cylindrical carbon composite core is 16 mm. The bending stiffness of the carbon composite material is one-third the bending stiffness of titanium-based surgical implant alloy and one-fifth the bending stiffness of cobalt-based surgical implant alloy. Cobalt-based surgical implant alloy possesses 1.7 times the bending stiffness of titanium-based surgical implant alloy. By considering second area moments of inertia of the cylindrical portion of the implant:

(a) A stem fabricated from either solid cobalt-based alloy or titanium alloy would have a second moment area of inertia $I = \pi D^4/64$ mm$^4$ = 1640 $\pi$ mm$^4$.

(b) A stem fabricated according to this invention with the outer component comprised of cobalt-based alloy would have a second moment area of inertia (equivalent in cobalt alloy) $I = \pi (D^4 - d^4)/64$ mm$^4$ + $\pi$ nd$^4$/64 mm$^4$ = 820 $\pi$ mm$^4$ (where n = the ratio of bending stiffness of the carbon material to that of the cobalt material = 1/5). Thus the composite filled cobalt alloy stem would possess 820 $\pi$ mm$^4$/1640 $\pi$ mm$^4$ = 0.5 the flexural rigidity of the solid cobalt alloy stem (a 2-fold difference).

(c) A stem fabricated according to this invention with the outer component comprised of titanium-based alloy would have a second moment area of inertia (equivalent in titanium alloy) $I = \pi (D^4 - d^4)/64$ mm$^4$ + $\pi$ nd$^4$/64 mm$^4$ = 957 $\pi$ mm$^4$ (where n = the ratio of bending stiffness of the carbon material to that of the titanium material = ⅓). Thus the composite filled titanium alloy stem would possess 957 $\pi$ mm$^4$/1640 $\pi$ mm$^4$ = 0.58 the flexural rigidity of the solid titaniium alloy stem.

(d) The flexural rigidity of the carbon composite core titanium alloy stem = EI = 957 $\pi$ Emm$^4$ (where E = Young's modulus in bending). The flexural rigidity of the conventional solid cobalt alloy sterm = EI = (1.7) 1640 $\pi$ Emm$^4$ = 2788 $\pi$ Emm$^4$. Thus, an implant fabricated according to this invention with a titanium alloy outer component and a carbon composite inner core would possess 957 $\pi$ Emm$^4$/2788 $\pi$ Emm$^4$ = 0.34 the flexural rigidity of a solid cobalt-based alloy stem (a 3-fold difference).

These gains in biomechanical compatibility may also be expressed in different terms. A 2-fold difference in flexural rigidity is about equivalent to the difference in flexural rigidities between a 15 mm and an 18 mm diameter solid metal stem. A 3-fold difference is about equivalent to the difference between solid metal stems that are 13.5 mm and 18 mm in diameter. Since the general surgical goal is to use an implant that will fill the intramedullary canal of the femur as much as possible, i.e., to use the largest stem possible in any given case, these differences in flexural rigidities are advantageous from the point of view of reducing the potential for stress-mediated bone loss.

It should be emphasized that the aforementioned theoretical differences in flexural rigidities of conventional solid metal implants and implants made according to this invention will vary in magnitude with stem size and the relative proportions of the outer and inner materials. The influence of stem diameter on the differences in flexural rigidities for stems ranging from 10 to 20 mm in diameter (in 2 mm increments) with a metal wall thickness of 1 mm is given in Table 1. The difference in flexural rigidity between a solid cobalt alloy stem and a stem with a titanium outer component and a carbon composite inner component ranges from 2.3-fold to 3-fold over the range of stem diameters commonly utilized in hip replacement surgery.

TABLE 1

Ratio of the bending stiffness of a solid surgical grade cobalt alloy stem ($C_s$) to that of a stem fabricated according to an embodiment of this invention with a surgical grade titanium alloy outer component and a carbon composite core ($T_{ccc}$).*

| Stem Diameter mm | Bending Stiffness Ratio ($C_s/T_{ccc}$) |
| --- | --- |
| 10 | 2.3 |
| 12 | 2.5 |
| 14 | 2.7 |
| 16 | 2.8 |
| 18 | 2.9 |
| 20 | 3.0 |

*Wall thickness of outer metal component = 1 mm. See the drawings.

It should be emphasized that the specifically disclosed embodiment of this invention may be extended to any joint implant with which implant fixation can benefit from an intramedullary or protruding stem. The biomechanical advantages and implant strength accured from this invention apply to any bone in which an implant is placed. The degree to which the implant is rendered hollow may vary from application to application. This will affect the degree to which the modified implant is rendered less flexurally rigid than the solid implant. The mechanical properties of the core material will also affect this parameter.

It should also be mentioned that the surgical procedures, per se, by which the novel prosthetic devices of the present invention are implanted in the patient are identical with those long known and practiced with surgical prosthetic devices of the prior art. See, e.g., Charles A. Engh and J. Dennis Bobyn, *Biological Fixation in Total Hip Arthroplasty*, Slack Inc., 1985, and especially Chapters 4 and 5.

What I claimed is:

1. An implantable composite prosthesis for replacement of a femoral hip joint comprising an elongated solid component defining a longitudinal axis and configured for insertion into a prepared intramedullary canal, said component being metallic and including an enlarged proximal region having a neck element extending medially outwardly from the longitudinal axis, said solid component having a substantially cylindrical hollow bore spaced a predetermined distance laterally from the neck element and extending along the longitudinal axis from the enlarged proximal region distally to a distal portion of the solid component; and a separate nonmetallic inner component complimentarily shaped to the hollow bore and disposed therein whereby the flexural rigidity of the composite prosthesis can be customized to fit the individual needs of the patient.

2. The composite prosthesis of claim 1 further including an end cap configured to be disposed within said hollow bore to enclose the inner component within the outer component.

* * * * *